US012751661B2

(12) United States Patent
Rao et al.

(10) Patent No.: US 12,751,661 B2
(45) Date of Patent: Oct. 6, 2026

(54) SYSTEM AND METHOD FOR CALIBRATING ELECTROOCULOGRAPHY SIGNALS BASED ON HEAD MOVEMENT

(71) Applicant: Massachusetts Institute of Technology, Cambridge, MA (US)

(72) Inventors: Hrishikesh Rao, Dedham, MA (US); Jeffrey S. Palmer, Westford, MA (US); Jason R. Nezvadovitz, Cambridge, MA (US)

(73) Assignee: Massacusetts Institute of Technology, Cambridge, MA (US)

( * ) Notice: Subject to any disclaimer, the term of this patent is extended or adjusted under 35 U.S.C. 154(b) by 317 days.

(21) Appl. No.: 18/557,615

(22) PCT Filed: Jun. 30, 2022

(86) PCT No.: PCT/US2022/035746

§ 371 (c)(1),
(2) Date: Oct. 27, 2023

(87) PCT Pub. No.: WO2023/278716

PCT Pub. Date: Jan. 5, 2023

(65) Prior Publication Data

US 2024/0206799 A1 Jun. 27, 2024

Related U.S. Application Data

(60) Provisional application No. 63/349,763, filed on Jun. 7, 2022, provisional application No. 63/217,485, filed on Jul. 1, 2021.

(51) Int. Cl.
*A61B 3/10* (2006.01)
*A61B 3/02* (2006.01)
(Continued)

(52) U.S. Cl.
CPC .............. *A61B 5/398* (2021.01); *A61B 3/113* (2013.01); *A61B 5/7221* (2013.01); *G06F 3/012* (2013.01);
(Continued)

(58) Field of Classification Search
CPC ......... A61B 3/02; A61B 3/102; A61B 3/1025; A61B 3/113; A61B 3/1015; A61B 3/1225; A61B 3/024; A61B 3/032; A61B 3/005
(Continued)

(56) References Cited

U.S. PATENT DOCUMENTS

| | | | | |
|---|---|---|---|---|
| 11,442,543 | B1 * | 9/2022 | Rai Kurlethimar | G06F 3/012 |
| 2012/0069301 | A1 * | 3/2012 | Hirata | A61B 5/4809 351/209 |
| 2016/0262608 | A1 | 9/2016 | Krueger | |
| 2018/0299953 | A1 | 10/2018 | Selker et al. | |
| 2019/0167095 | A1 | 6/2019 | Krueger | |

OTHER PUBLICATIONS

PCT International Search Report and Written Opinion dated Dec. 6, 2022, for International Application No. PCT/US22/35746; 8 pages.
(Continued)

*Primary Examiner* — Dawayne Pinkney
(74) *Attorney, Agent, or Firm* — Daly, Crowley, Mofford & Durkee, LLP

(57) ABSTRACT

A method for calibrating eye information includes receiving eye state data measured during a calibration period, receiving head state data measured during the calibration period, calibrating the eye state data based on the head state data, and generating an eye angle measurement based on the calibrated eye state data. Calibrating the eye state data may include correlating the eye state data with the head state data during a period when a vestibulo-ocular reflex occurs. In some implementations, the eye state data may include eye movement data and the head state data may include head
(Continued)

movement data. The calibrated eye state data is considered to have improved accuracy and therefore may be used as a more reliable basis for determining a variety of health conditions.

20 Claims, 10 Drawing Sheets

(51) Int. Cl.

| | |
|---|---|
| ***A61B 3/024*** | (2006.01) |
| ***A61B 3/113*** | (2006.01) |
| ***A61B 3/12*** | (2006.01) |
| ***A61B 5/00*** | (2006.01) |
| ***A61B 5/398*** | (2021.01) |
| ***G06F 3/01*** | (2006.01) |

(52) U.S. Cl.
CPC ...... *G06F 3/013* (2013.01); *A61B 2560/0223* (2013.01)

(58) Field of Classification Search
USPC ....... 351/205, 200, 206, 209, 210, 221–223, 351/237, 243, 245, 246
See application file for complete search history.

(56) References Cited

OTHER PUBLICATIONS

Vidal et al., "Analysing EOG Signal Features for the Discrimination of Eye Movements with Wearable Devices"; Lancaster University; PETMEI '11, Sep. 18, 2011; 6 pages.
Barbara et al., "EOG-Based Ocular and Gaze Angle Estimation Using an Extended Kalman Filter"; Symposium on Eye Tracking Research and Applications (ETRA '20 Short Papers), Jun. 2-5, 2020 in Stuttgart, Germany; 5 pages.
Barbara et al., "EOG-Based Gaze Angle Estimation Using a Battery Model of the Eye"; 2019 41st Annual International Conference of the IEEE Engineering in Medicine and Biology Society (EMBC), Jul. 2019 in Berlin, Germany; 4 pages.
Manabe et al., "Direct Gaze Estimation Based on Nonlinearity of EOG"; IEEE Transactions on Biomedical Engineering, vol. 62, No. 6; Jun. 2015; 10 pages.
Hirvonen et al., "A comparison of static and dynamic calibration techniques for the vestibulo-ocular reflex signal"; International Journal of Clinical Monitoring and Computing, 12; May 1995; 6 pages.
Mansson et al., "A New and Simple Calibration of the Electro-Ocular Signals for Vestibulo-Ocular Measurements"; Aerospace Medical Association; Aviation, Space, and Environmental Medicine; Sep. 1987; 6 pages.

* cited by examiner

SYSTEM AND METHOD FOR CALIBRATING ELECTROOCULOGRAPHY SIGNALS BASED ON HEAD MOVEMENT

CROSS REFERENCE TO RELATED APPLICATIONS

This application is a National Stage Entry of International Application No. PCT/US2022/035746, which was filed on Jun. 30, 2022, which claims priority to and the benefit of U.S. Provisional Patent Application No. 63/349,763, which was filed on Jun. 7, 2022, and U.S. Provisional Patent Application No. 63/217,485, which was filed on Jul. 1, 2021. The entire contents of these applications are incorporated herein by reference.

STATEMENT REGARDING FEDERALLY SPONSORED RESEARCH

This invention was made with government support under FA8702-15-D-0001 awarded by the U.S. Air Force. The government has certain rights in the invention.

FIELD

One or more embodiments described herein relate to processing information including, but not limited to, calibrating electrooculography signals based on head movement.

BACKGROUND

Electrooculography refers to methods of determining eye movement based on electrical signals sensed by electrodes at certain points around the eye. The signals are processed in the form of an electrooculogram and serve as a basis for gaining insight into physiological status, cognitive state, neurological function, and/or other health conditions.

An alternative to electrooculography is to track eye movement via infrared video of the eye. These methods have a number of short-comings including a bulky form factor, substantial power consumption, high on-board image processing computational requirements, susceptibility to motion artifacts, and sensitivity to error through dynamic environmental lighting.

Whether performed based on electrical signals or infrared video, existing electrooculographic methods must be performed by health professionals in a controlled medical setting such as a diagnostic center, doctor's office, or hospital. They are constrained to acquiring measurements for a discrete period of time, when the subject is not behaving as he or she normally would at home or under other normal living conditions. Moreover, existing electrooculographic and infrared video methods are unsuitable for use in mobile environments or rugged field conditions, such as when a test subject is walking, driving, or engaging in other everyday activities. For these and other reasons, existing electrooculographic and infrared video methods do not provide an indication of eye movement in so-called free-living conditions, making them impractical as a preventative health tool and for real-time monitoring applications.

SUMMARY OF THE INVENTION

In accordance with one aspect of the concepts, system and methods described herein, it has been recognized that EOG is of limited use without calibration and has been underutilized. Currently, such calibration can only be carried out in a controlled/laboratory setting. Thus, existing EOG systems and methods are unsuitable for use in "free-living" or "field" conditions (i.e., use of EOG during a person's everyday living environment and activities without the need for in a calibration in a controlled/laboratory setting). That is, while existing EOG systems/methods are capable of detecting electrical signals related to eye movement in field conditions (e.g. even rugged field conditions), there currently is no way to calibrate such electrical signals into meaningful information.

In accordance with a further aspect of the concepts, system and methods described herein, an EOG calibration method includes calibrating eye state data based on head state data acquired during a time when a subject is performing a vestibulo-ocular reflex (VOR) and continuously performing calibration regardless of whether a VOR is occurring With this particular arrangement EOG calibration may be performed in free-living conditions.

In accordance with one or more embodiments, a system and method are provided for calibrating eye state data based on head state data during a time when a vestibulo-ocular reflex is taking place in a subject. This may be accomplished by effectively combining (or fusing) the eye state data and head movement data to produce a consistent angular representation of eye movements, thereby enabling the collection of high quality eye movement data in free-living conditions over long periods of time.

In accordance with one embodiment, a method for processing information includes receiving eye state data measured during a calibration period; receiving head state data measured during the calibration period; calibrating the eye state data based on the head state data; and generating an eye angle measurement based on the calibrated eye state data, wherein calibrating the eye state data includes correlating the eye state data with the head state data based on any vestibulo-ocular reflex (VOR) that occurs. In embodiments, calibrating the eye state data includes correlating the eye state data with the head state data based on any VOR that occurs while viewing a target. In general use, however, it doesn't matter why the VOR is engaged, just that it is (it is noted that a person's VOR engages when their gaze is fixated on anything while their head moves, e.g. while looking at a person you're saying "hi" to while walking passed them).

In accordance with one or more embodiments, a system for processing information includes a storage area configured to store instructions and a processor configured to execute the instructions to: receive eye state data measured during a calibration period; receive head state data measured during the calibration period; calibrate the eye state data based on the head state data; and generate an eye angle measurement based on the calibrated eye state data, wherein the processor is configured to calibrate the eye state data by correlating the eye state data with the head state data based on any vestibulo-ocular reflex that occurs.

A system of one or more computers can be configured to perform particular operations or actions by virtue of having software, firmware, hardware, or a combination of them installed on the system that in operation causes or cause the system to perform the actions. One or more computer programs, which may be stored on non-volatile storage media, can be configured to perform particular operations or actions by virtue of including instructions that, when executed by data processing apparatus, cause the apparatus to perform the actions. Some or all of the actions described below may be performed by a computer executing software instructions, by hardware, or by a combination of a computer executing software instructions and hardware.

One general aspect includes a method for processing information. The method also includes receiving eye state data measured during a calibration period; receiving head state data measured during the calibration period, continuously calibrating the eye state data based on the head state data, and generating an eye angle measurement based on the calibrated eye state data, where calibrating the eye state data includes correlating the eye state data with the head state data based on a vestibulo-ocular reflex that occurs while viewing a target.

Implementations may include one or more of the following features. The method where: the eye state data includes eye movement data; and the head state data includes head movement data. Correlating the eye movement data includes: implementing at least one probabilistic model to correlate the eye state data measured during the calibration period with the head state data. The head state data includes gaze information, and the eye state data includes calibration coefficients corresponding to eye state. Continuously generating the eye state data includes: (a) generating a first probability distribution based on one or more initial values of the head state data and data from a head sensor; (b) generating a second probability distribution based on initial values of the eye state data; (c) generating estimates of gaze and the calibration coefficients based on the first probability distribution and the second probability distribution; and (d) iteratively repeating (a) to (c) with the first probability distribution generated based on the estimate of the gaze generated in (c). The first probability distribution is generated using a VOR rotational model. Continuously generating the eye state data includes: generating an expected electrooculogram (EOG) based on the first probability distribution and the second probability distribution; comparing the expected EOG with an actual EOG; generating error data based on the comparison; and generating the estimates of gaze and the calibration coefficients based on the first probability distribution, the second probability distribution, and the error data. Generating the estimates of gaze and the calibration coefficients is performed by a Bayesian updating method.

One general aspect includes a system for processing information. The system also includes a storage area configured to store instructions; and a processor configured to execute the instructions to: receive eye state data measured during a calibration period; receive head state data measured during the calibration period; continuously calibrate the eye state data based on the head state data; and generate an eye angle measurement based on the calibrated eye state data, where the processor is configured to calibrate the eye state data by correlating the eye state data with the head state data based on a vestibulo-ocular reflex that occurs.

Implementations may include one or more of the following features. The system where: the eye state data includes eye movement data; and the head state data includes head movement data. The processor is configured to correlate the eye movement data by implementing at least one probabilistic model to correlate the eye state data measured during the calibration period with the head state data. The head state data includes gaze information, and the eye state data includes calibration coefficients corresponding to eye state. The processor is configured to continuously generate the eye state data by: (a) generating a first probability distribution based on one or more initial values of the head state data and data from a head sensor; (b) generating a second probability distribution based on initial values of the eye state data; (c) generating estimates of gaze and the calibration coefficients based on the first probability distribution and the second probability distribution; and (d) iteratively repeating (a) to (c) with the first probability distribution generated based on the estimate of the gaze generated in (c). The processor is configured to generate the first probability distribution using a VOR rotational model. The processor is configured to continuously generate the eye state data by: generating an expected electrooculogram (EOG) based on the first probability distribution and the second probability distribution; comparing the expected EOG with an actual EOG; generating error data based on the comparison; and generating the estimates of gaze and the calibration coefficients based on the first probability distribution, the second probability distribution, and the error data. The processor is configured to generate the estimates of gaze and the calibration coefficients is performed by a bayesian updating method.

One general aspect includes a non-transitory computer-readable medium storing instructions. The instructions also include receiving eye state data measured during a calibration period; receiving head state data measured during the calibration period; continuously calibrating the eye state data based on the head state data; and generating an eye angle measurement based on the calibrated eye state data, where calibrating the eye state data includes correlating the eye state data with the head state data based on a vestibulo-ocular reflex that occurs while viewing a target.

Implementations may include one or more of the following features. The medium where: the head state data includes gaze information, and the eye state data includes calibration coefficients corresponding to eye state. The instructions, when executed by the one or more processors, cause the one or more processors to: (a) generate a first probability distribution based on one or more initial values of the head state data and data from a head sensor; (b) generate a second probability distribution based on initial values of the eye state data; (c) generate estimates of gaze and the calibration coefficients based on the first probability distribution and the second probability distribution; and (d) iteratively repeat (a) to (c) with the first probability distribution generated based on the estimate of the gaze generated in (c). The instructions, when executed by the one or more processors, cause the one or more processors to: generate an expected electrooculogram (EOG) based on the first probability distribution and the second probability distribution; compare the expected EOG with an actual EOG; generate error data based on the comparison; and generate the estimates of gaze and the calibration coefficients based on the first probability distribution, the second probability distribution, and the error data.

DETAILED DESCRIPTION

Embodiments described herein correspond to a system and method for calibrating eye state data based on head state data acquired during a time when a subject is performing a vestibulo-ocular reflex. The calibration may be continuously performed throughout a calibration period, and in some embodiments at other times when, for example, a vestibulo-ocular reflex is not occurring. Because the eye state data is continuously calibrated in this manner, the eye state data generated by the system and method may have improved accuracy and may also provide a basis for generating eye angle measurements with greater reliability. This, in turn, may increase the efficacy of determining physiological status, cognitive state, neurological function, and/or other health conditions.

Figure 1A:
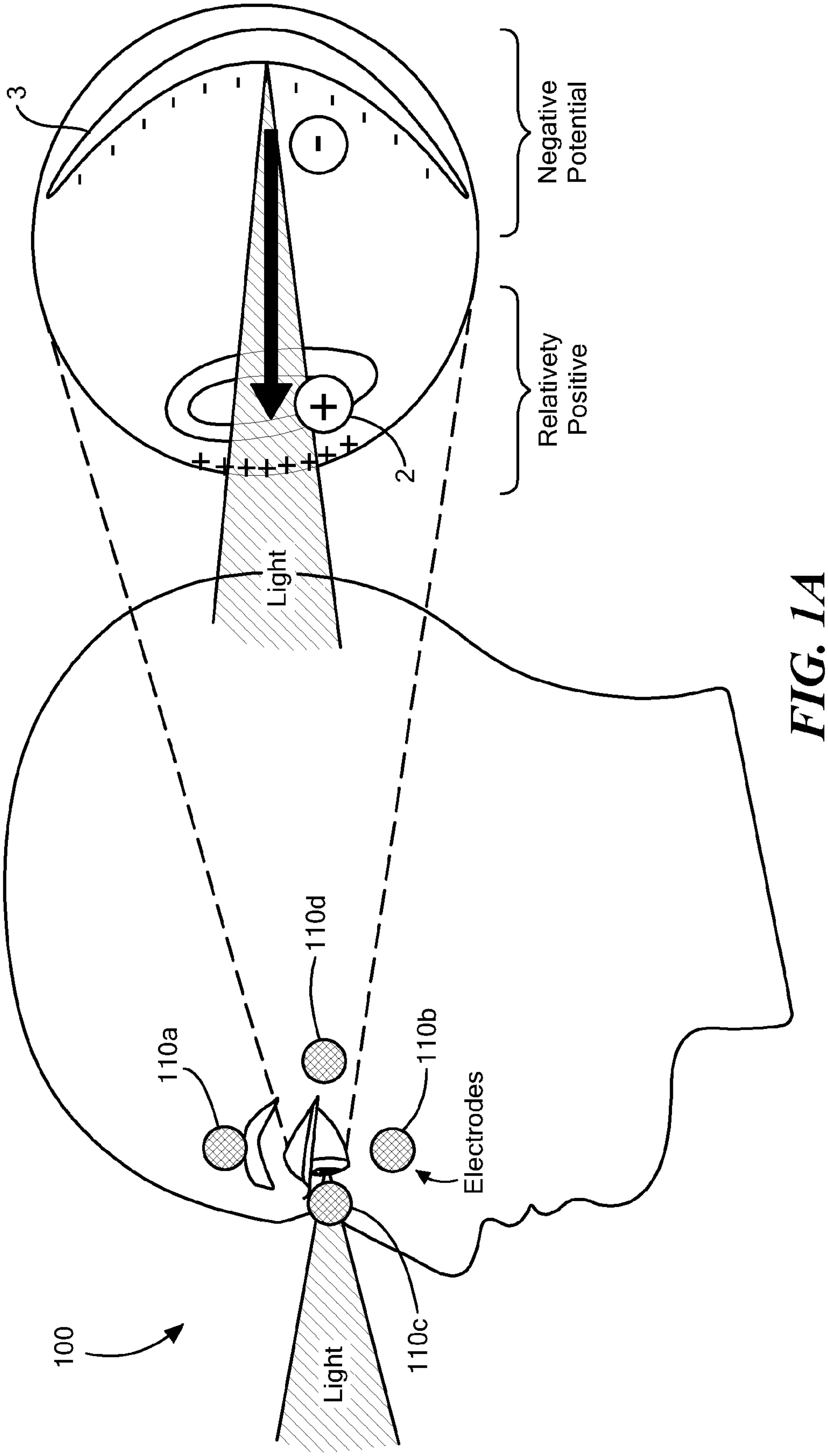
FIG. 1A shows an example of a electrooculography sensors.
Figure 1B:
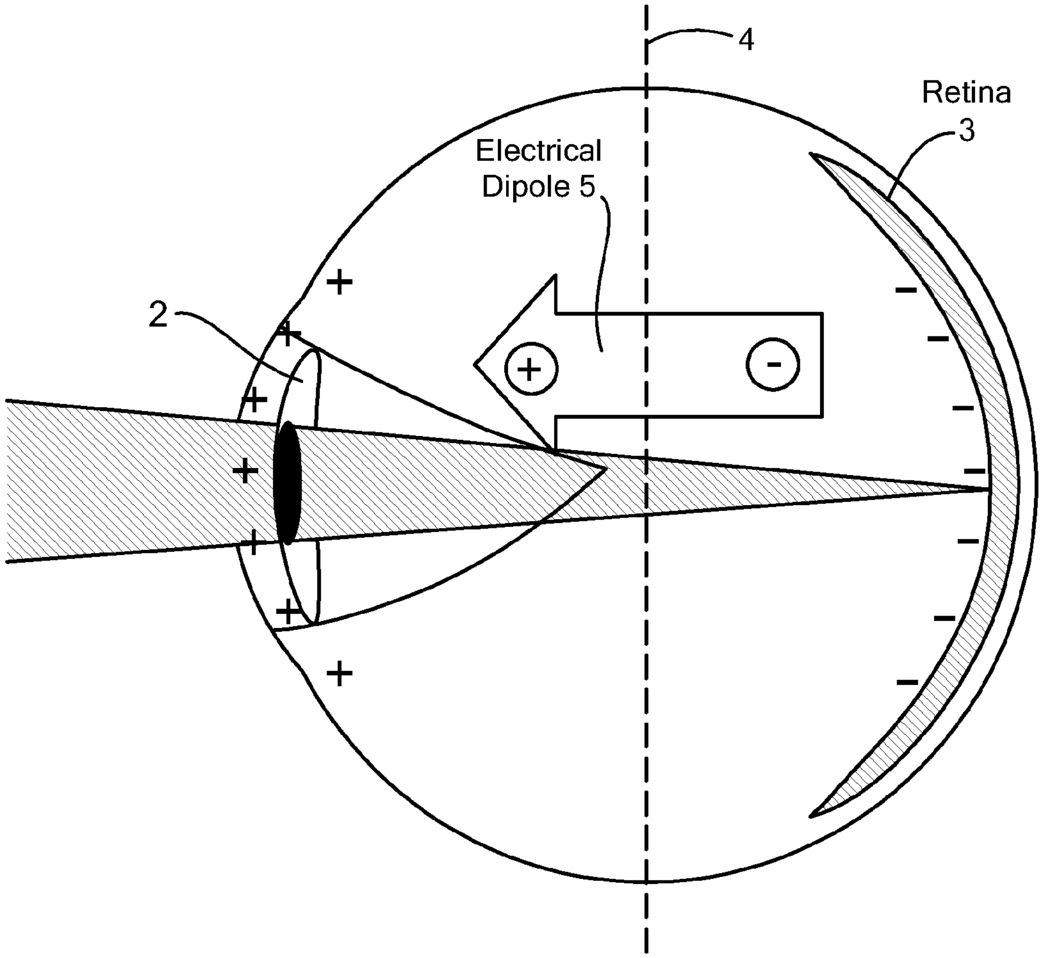
FIG. 1B shows an example of electrical dipole generation.

FIG. 1A shows an example of a measurement system 100 which may be used to acquire eye state data from a subject. The eye state data may include electrooculography (EOG) data and/or another type of eye state data (e.g. video eye tracking data). The system includes one or more sensors arranged at predetermined locations in an area proximate to an eye under observation. In this example, four sensors in the form of surface electrodes 110*a* to 110*d* are adhered or otherwise disposed on the skin in the eye area to measure the standing electrical potentials between the front (lens) 2 and the back (retina) 3 of the eye. The electric potentials may form an electrical dipoles 5 (e.g., as shown in FIG. 1B) and may be used as a basis for generating EOG signals indicative of eye state, including but not limited to eye position and/or eye movement. In another embodiment, a different number and/or arrangement of sensors may be disposed around the eye or other locations of the head for generating EOG signals. One possible alternative head location is around the ear.

The electrical potential values measured or otherwise acquired via the electrodes may lie in one of at least two ranges, for example a first range having positive potential values and a second range having negative potential values. The sign of the values (positive or negative) may be determined, for example, relative to a reference line 4 (FIG. 1B) passing through the center of the eyeball. In operation, light enters the eye and the electrodes 110*a* to 110*d* output changing potentials (or voltages) indicative of eye state, e.g., position and/or movement (rotation) of the eye. These electrical signals may be received no matter where the subject is looking, and the voltages may change whenever the eye of the subject moves at all. An example of the changing voltages generated by a four-electrode arrangement is shown in FIGS. 2A to 2C.

Figure 2A:
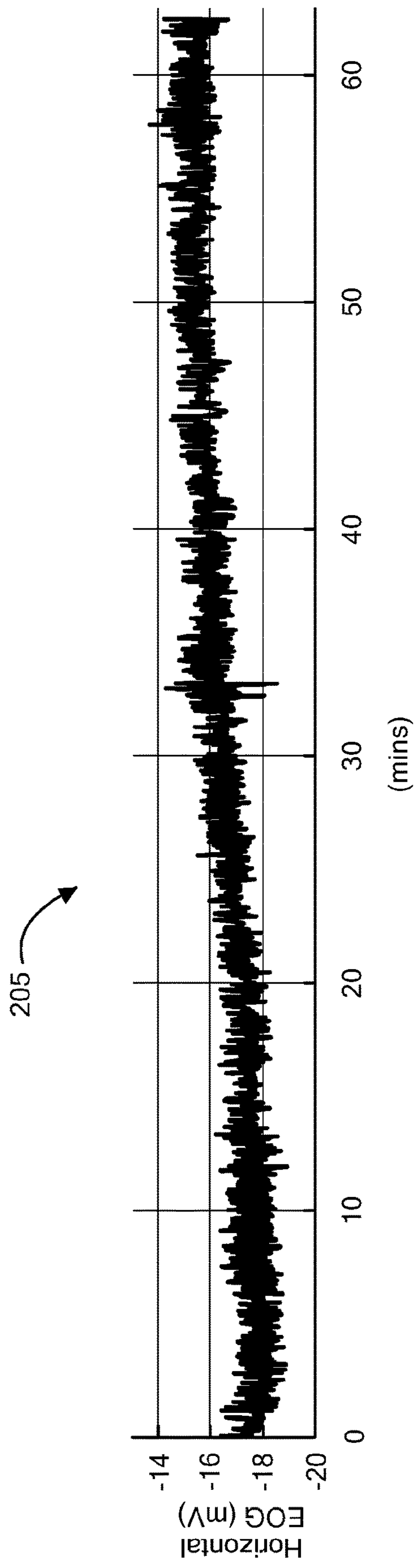
FIGS. 2A to 2C show examples of raw eye data signals.

FIG. 2A shows an example of a raw EOG signal 205 (i.e. an EOG signal which has not been processed or filtered) output from one or more of the electrodes over a time period of 60 minutes. As shown, the magnitude of the signal varies as a result of the position of the electrodes relative to the eye, individual physiological variability, changes in electrode-skin impedance, changes in retinal activity (e.g. intensity of ambient light), and/or other factors. This raw signal acquired can correspond to different pairs of the surface electrodes.

Figure 2B:
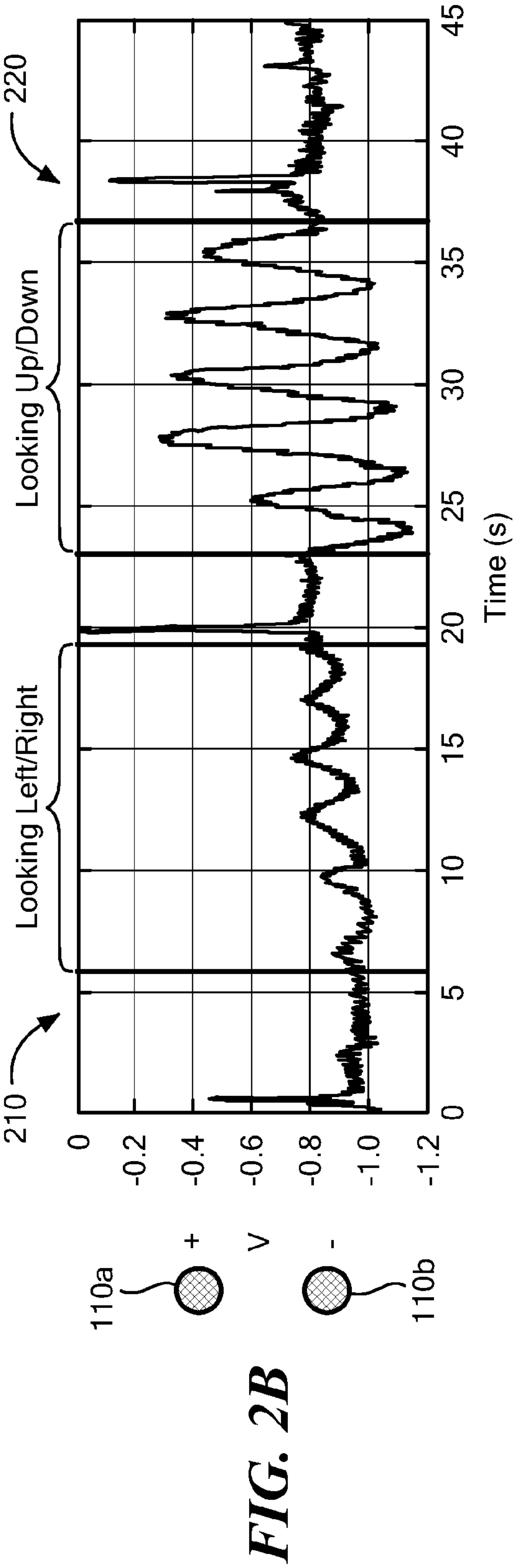
Figure 2C:
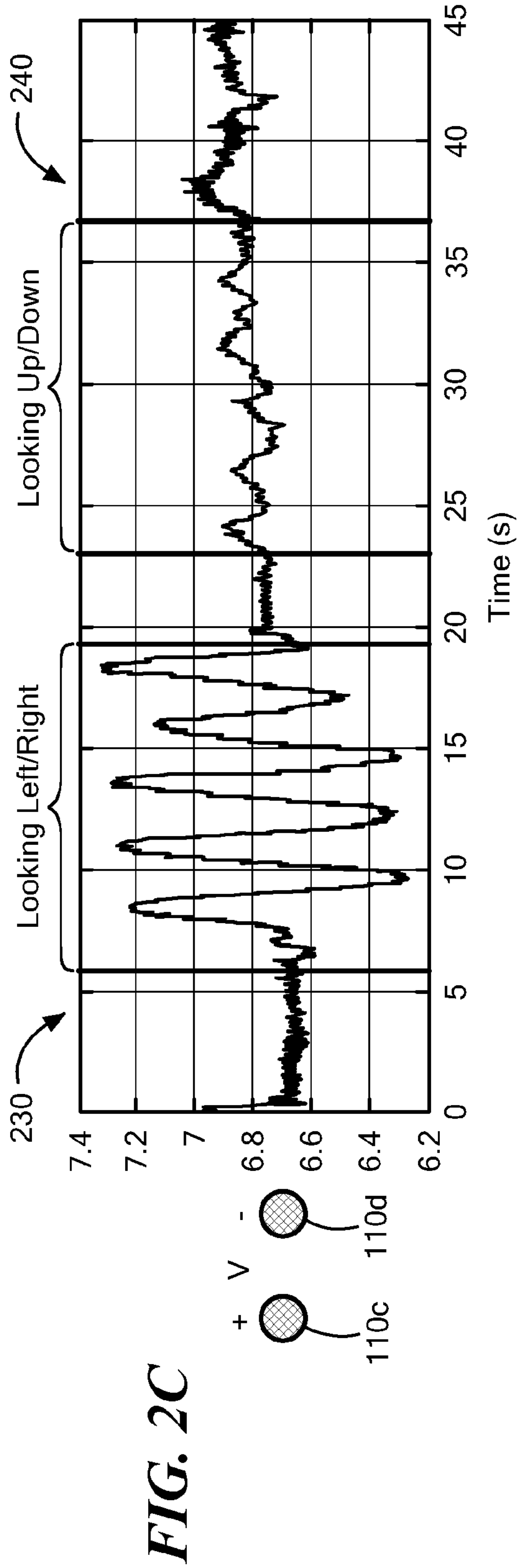

FIG. 2B shows an example of the changing voltage signals produced by a first opposing pair of electrodes 110*a* and 110*b*, e.g., the pair of electrodes that are vertically arranged relative to the eye shown in FIG. 1. The changing voltage signals are partitioned into two sections based on different head states of the subject. The head states may include, for example, head position, head orientation, and/or head movement (including lack of movement, e.g. stationary). In embodiments, position may be represented as "x/y/z" positions in a Cartesian coordinate system and head orientation may be represented as "roll/pitch/yaw" at a given position. Other coordinate systems including but not limited to Polar and Cylindrical coordinate systems may, of course, also be used. The calibration systems and techniques described herein may be used regardless of the representation of type of s head position and head orientation.

In one embodiment, the first section 210 corresponds to when the subject moves his or her head laterally, e.g., up or down. In this case, the voltages output by the electrodes 110*a* and 110*b* vary with a first frequency range and in a first amplitude range in the time period corresponding to first section 210. The second section 220 corresponds to when the subject moves his or her head right or left. In this case, the voltages output from the electrodes 110 of the first pair vary in a second frequency range and in a second amplitude range. The voltages in the first and second amplitude ranges are absolute magnitudes of the EOG signals.

Thus, FIG. 2B may illustrate at least three salient points: (1) electrodes 110*a* and 110*b* are ideally suited to measuring vertical movement of the eye, and thus large changes in voltage may be observed when the person is looking up/down; (2) electrodes 110*c* and 110*d* may be better suited to measure horizontal eye movements, and thus there may be more electrical potential change when the person looks left/right; and (3) the set of electrodes may not generate as much potential change in the directions in which they are not suited to measure (e.g., little activity in time 240 for 110*c* and 110*d*).

FIG. 2C shows an example of the changing voltage signals produced by a second opposing pair of electrodes 110*c* and 110*d*, e.g., the pair of electrodes that are horizontally arranged relative to the eye shown in FIG. 1. The changing voltage signals are partitioned into two sections based on different head movements of the subject. The first section 230 corresponds to when the subject moves his or her head laterally, e.g., left-to-right or vice versa. In this case, the voltages output by the electrodes 110*c* and 110*d* vary with a third frequency range and in a third amplitude range in the time period corresponding to first section 230. The second section 240 corresponds to when the subject moves his or her head up and down. In this case, the voltages output from the electrodes 110*c* and 110*d* vary in a fourth frequency range and in a fourth amplitude range. The voltages in the third and fourth amplitude ranges are absolute magnitudes of the EOG signals.

The absolute magnitudes of the voltage signals output from the electrodes can be arbitrary and variable due to one or more factors. These factors include, but are not limited to, variable bio-potentials that naturally vary among individuals, varying locations of electrode placement relative to the eye, changes in impedance of the electrodes over time due, for example, to drying or the formation of sweat under the electrodes, varying environmental lighting conditions, as well as the adapted state of the retina (e.g., light- or dark-adapted). Relative changes in the magnitudes of the electrode voltages convey at least some meaningful information, e.g., whether or not an eye movement happened and the time at which the movement occurred.

However, this information alone is unable to indicate how or in what manner or to what extent eye movement took place. For example, the absolute magnitude of eye movement (e.g., true degree of rotation) may not be determined without a mapping between voltage and rotational degree. The true rotation of the eye (in degrees rather than relative voltage) may serve as a physically consistent measure to compare across subjects and time, and may also be used as a basis for performing subsequent analysis to determine physiological, cognitive, neurophysiological, and/or other types of medical and health conditions. Providing an indication of eye movement, angle of eye movement, magnitude of eye movement, time of eye movement, etc., may allow this subsequent these subsequent types of analyses to be performed.

The relative voltages derived from the EOG electrodes may be converted to eye rotation degree values using various approaches. One approach involves an angular reference calibration. During this process, a subject looks at specific, pre-designated points on a screen. Measured changes in electrode voltage are then correlated with the rotation amplitude of the eye. The rotation amplitude may be calculated based on the positions and known, predetermined spacings of the points. However, this angular reference calibration approach requires the use of additional equipment (e.g., cameras, head-rests, etc.) more than just the EOG electrodes. This additional equipment increases costs and computational complexity and limits utility to laboratory settings. Additionally, changes in electrode impedance on the skin over time may invalidate the original calibration. In order to guard against these effects, regular re-calibration may be performed in an attempt to maintain a consistent, accurate representation of eye angle, at least to the extent possible using this approach. These and other challenges may reduce the practicality of EOG applications and have made them unsuitable for mobile, long-duration use.

Figure 3:
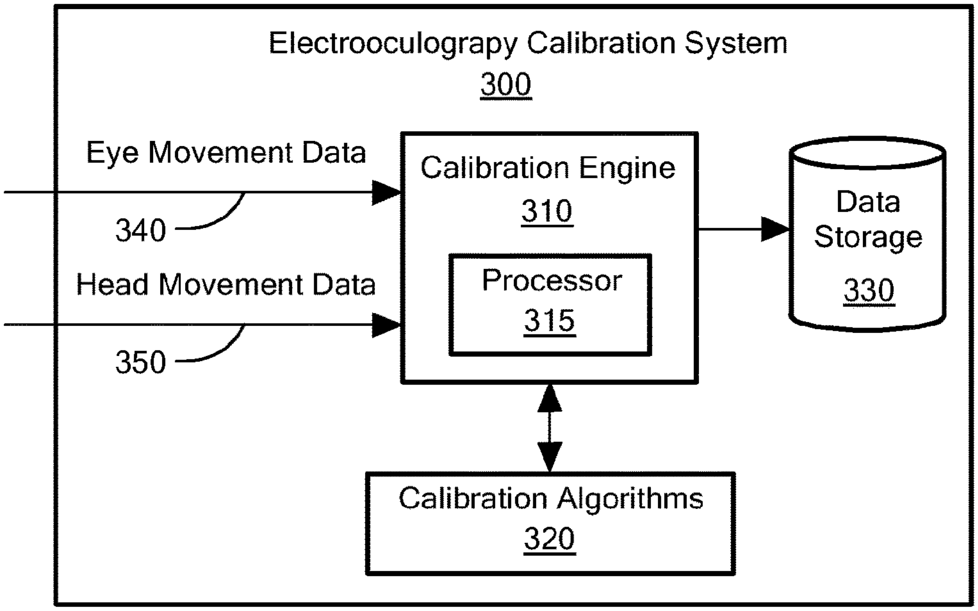
FIG. 3 shows an embodiment of a system for calibrating eye state data.

FIG. 3 shows an embodiment of a system 300 for calibrating eye state data. The eye state data may correspond to electrooculography (EOG) data, but in other implementations may correspond to video tracking data or another type of data. For purposes of illustration, some embodiments where the eye state data is based on EOG signals are described below. In FIG. 3, the calibration algorithms are shown to be outside of the calibration engine. However, this is just an illustration. In some embodiments, the calibration engine may include the calibration algorithms, e.g., box 320 may also be included in box 310.

Referring to FIG. 3, the system includes a calibration engine 310, a memory 320, and a storage area 330. The calibration engine 310 may include or be implemented by one or more processors 315 that perform operations for calibrating data from the sensor equipment, which, for example, may include the arrangement electrodes 110*a* to 110*d* shown in FIG. 1 or in embodiments to be described in greater detail below. The equipment may also include a gyroscope or another type of head state sensor. For purposes of illustration, the calibration operations will be discussed as being performed by one processor 315.

Processor 315 may perform calibration by implementing various algorithms (or models) for processing eye state data and/or head state data in a way that fuses the two together and/or modifies the eye state data based on the head state data for calibration. In one embodiment, the calibration processing involves continuously linking (or fusing) the eye state data with the head state data using an iterative approach, in order to generate calibrated eye state data. The calibrated eye state data may, in turn, may be used to generate eye angle measurements automatically and with a high degree of precision, all without requiring the use of eye trackers or other types of additional equipment.

The eye state data may be indicative of eye position, orientation, movement (including a state where the eye is not moving), and/or blinks during the calibration period. The head state data may be indicative of head position, orientation, and/or movement (including a state where the head is not moving) during the calibration period. For illustrative purposes, examples are discussed where the eye state data corresponds to electrooculography data and the head state data corresponds to head angular movement data. In some implementations the processor of calibration engine 310 may produce a consistent angular representation of eye movements, which enable the collection of high quality eye movement data in free-living conditions, in mobile applications, and/or over long periods of time in areas inside or outside of a medical facility. Embodiments of the types of processing performed by the calibration engine and its models are described in greater detail below.

The memory 320 stores instructions which, when executed by the processor 315 of the calibration engine, perform the types of processing described herein. The instructions may include, for example, software, firmware, or other types of instructions executable by a processor for implementing the calibration models (and algorithms). In one embodiment, the models may be partitioned into stages, for example, based on the type of processing to be performed and/or the type of data to be processed. As will be described in greater detail below, one stage may be a prediction stage and another stage may be an update step stage. Although these are merely examples, the calibration engine may include another arrangement of stages or models in other embodiments. The memory 320 may be a non-transitory computer-readable medium for storing the instructions for the calibration engine. The computer-readable medium may be, for example, a type of read-only or random access memory.

The storage area 330 may store the calibrated eye state data output from the calibration engine for archival purposes and/or for access by one or more healthcare or research professional for performing, for example, subsequent analysis, including but not limited to performing a medical, psychological, or health evaluation. The storage area 330 may be any of the types of computer-readable media used to implement memory 320, or may be a centralized or decentralized database, an archive, or another type of storage area.

While the techniques implemented via the calibration engine may vary, in one or more embodiments the techniques may be used to link predetermined relationships between eye movement data and head movement data to generate calibrated eye movement data automatically and continuously during the calibration period. The calibration period may include, for example, a period when the subject is experiencing a vestibulo-ocular reflex (VOR), whether that period is in a clinical setting or a free-living or other setting at home, work, or any other type of free-living environment.

Figure 4:
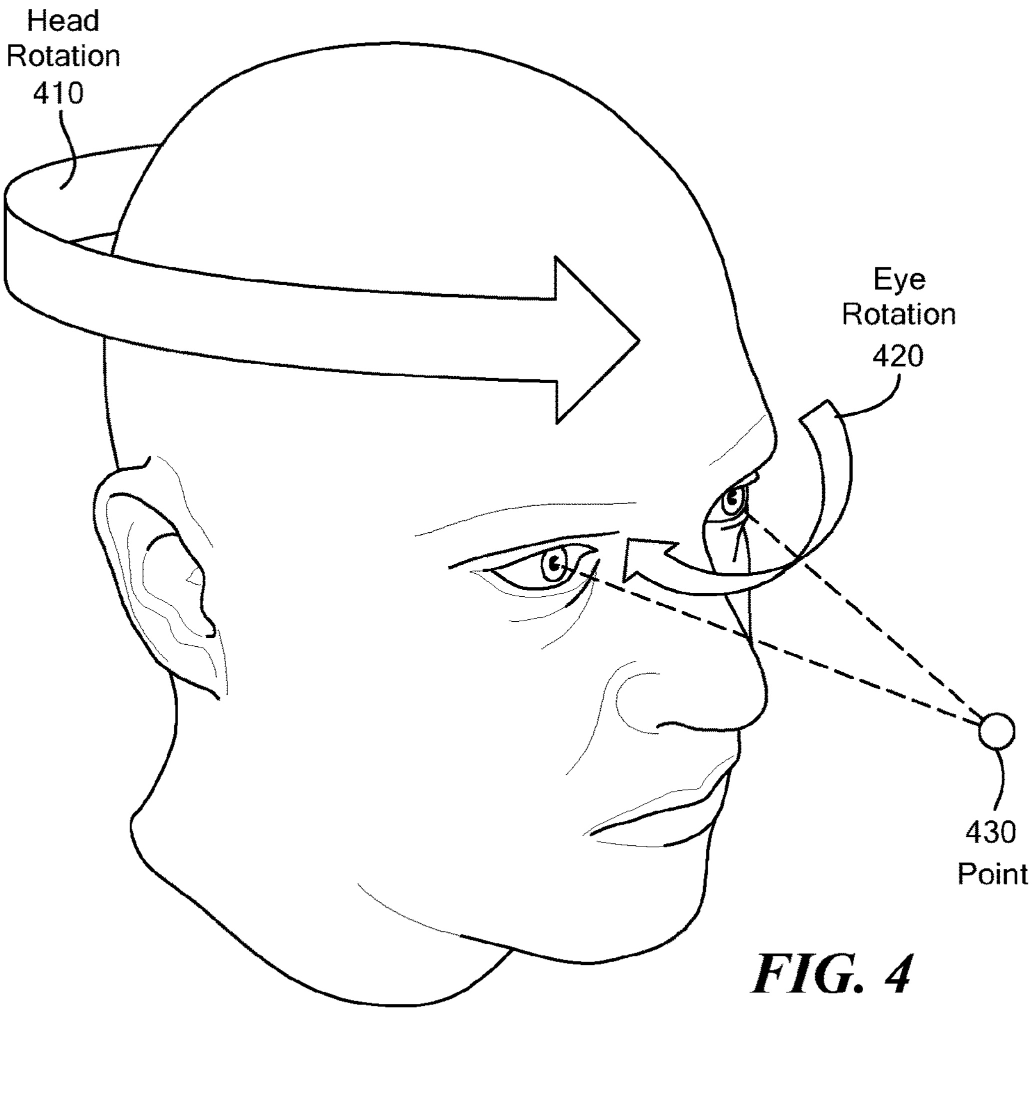
FIG. 4 shows an example of a vestibulo-ocular reflex.

FIG. 4 shows an example of a vestibulo-ocular reflex (VOR) that may take place in a test subject viewing any location or point 430 in space during a calibration period. During VOR, when the head rotates (arrow 410), the eyes of the subject rotate in the opposite direction (arrow 420) to allow the subject to continue to look at point 430 (e.g., a target or other point of focus). The relationship that takes place between head and eye movements during VOR is highly stereotyped in direction, magnitude, and timing and, for example, may be determined on this basis. In one embodiment, the relationship between head and eye movements may be determined on through experimentation or through trials performed on a subject-by-subject basis.

Irrespective of how the head movement data is acquired, the head movement (rotation) data generated during VOR may be used as a basis for calibrating eye movement data in a manner that is more accurate than other methods. Put differently, by measuring the rotations of the head while the VOR is engaged, the expected rotations of the eye can be related to the measured EOG response to consistently calibrate the EOG. Moreover, the calibrated eye movement data may be used as a basis for generating a more accurate eye angle measurement, which, in turn, may provide a more reliable indication of the health condition of the subject. In embodiments, a user wouldn't have to actively perform VOR (e.g. as may be done in a lab or controlled setting) rather, the measurements and calibration processing occur during free-living. That is, the systems and methods described herein allow a user to have a "wear-and-forget" experience (VOR is being detected when it occurs and continuous calibration may occur during the period of wearing).

In the example of FIG. 4, the rotational head and eye movement is shown to be lateral. However, in another embodiment the rotational head and eye movement may follow a vertical, diagonal, or random pattern. As previously indicated, rotation of the head can be measured, for example, during a calibration period using a tiny, low-cost, low-power gyroscope, making the whole arrangement non-intrusive, of low size and weight, and able to exhibit low power consumption.

Figure 5A:
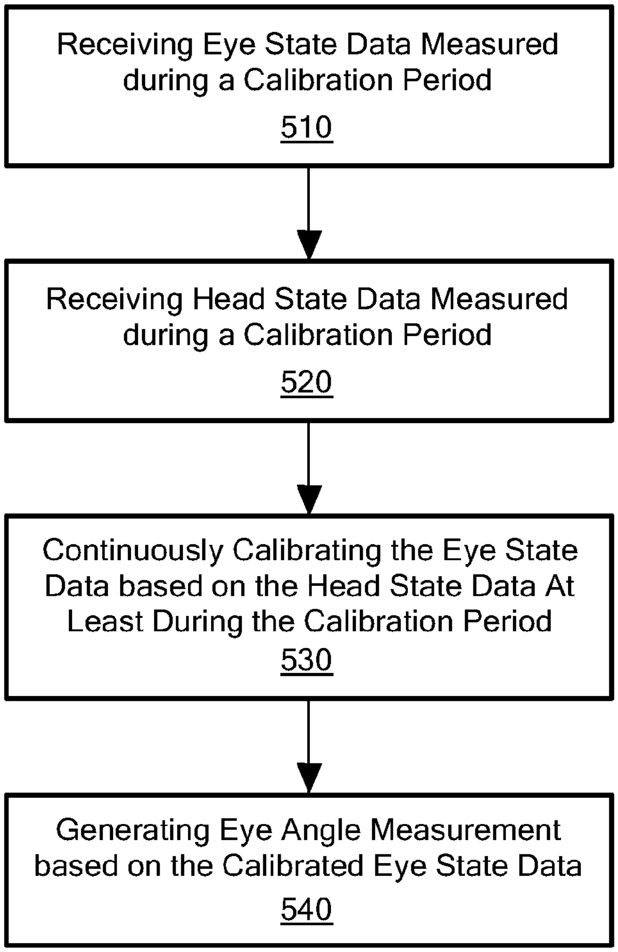
FIG. 5A shows an embodiment of a method for calibrating eye state data.

FIG. 5A shows a flow chart representing an embodiment of a method of calibrating eye state data based on head state data acquired during a period when a vestibulo-ocular reflex is taking place. The method may be performed, for example, by any of the system or apparatus embodiments described herein. For purposes of illustration, the method embodiment of FIG. 5 will be described as being performed by the calibration engine 310 of FIG. 3, as a result of processor 315 executing algorithm instructions stored in memory 320.

As previously indicated, the eye state data may correspond to eye position data, eye movement data, or both. The eye state data may indicate whether or not the eye is moving or stationary. Also, the head state data may correspond to head position data, head movement data, or both. The head state data may indicate whether or not the head is moving or stationary. For illustrative purposes only, the eye state data and the head state data will be described as eye movement data and head movement data, respectively.

The method represented in FIG. 5A includes, at 510, receiving eye movement data measured during a predetermined period, which, for example, may be at least the calibration period. The eye movement data may include or be based on EOG signals (e.g., voltages) output from one or more eye sensors, for example, which may correspond to surface electrodes 110*a* to 110*d* shown in FIG. 1. The EOG signals are indicative of eye orientation. In embodiments, eye movement data resultant from or generated by any type of eye movement tracking system (e.g. infrared video) may be used.

In one embodiment, the eye movement data may be output continuously over the calibration period. In another embodiment, the eye movement data may be output at predetermined times during the calibration period and/or may be event driven, e.g., triggered when one or more predetermined events occurs. Examples of these events include, but are not limited to, inertial detection of a rotation of the head.

At 520, head movement data measured during the calibration period is received from one or more sensors, e.g. a gyroscope. The head movement data is generated as VOR takes place with the eye movement, so that the head movement data can be correlated to the eye movement data in subsequent operations as described herein. The head movement data may include head rotation data and, for example, may be measured using a gyroscope as previously described. In one embodiment, the calibration engine 310 may receive a detection signal indicating that VOR is taking place. When the detection signal is received, processor 315 may execute the algorithms to generate calibrated eye movement data. In some cases, the processor may continue to execute the algorithms during times in the calibration period where VOR is not taking place. It should be appreciated that the processing which takes place in blocks 510 and 520 may take place at the same time or in any order.

The calibration engine may determine when VOR is taking place in various ways. One way involves detecting periods of high negative correlations between eye and head rotation. High negative correlations may correspond, for example, to negative correlations that exceed a predetermined threshold. If the eye and head rotations are happening for the same duration but in opposite directions, the engine (or other processing logic) can conclude that the period was a period of VOR.

Another approach involves use of a recursive Bayes algorithm, for example, as discussed in the update stage below. In this case, "whether or not VOR is enabled" is treated as another "state variable" whose probability distribution may be (approximately) computed. Unlike other variables that are to be estimated, this variable may be discrete/binary. The probabilistic inference would essentially do what the above approach does, but is "tightly coupled" to the rest of the estimation. For example, the state of "detection of VOR" may not be separated from the state of "estimation of calibration." Rather, these states may occur simultaneously and with maximally efficient information sharing.

For example, if the EOG voltage is moving in a way that looks counter to the head movement, it may not always be the case that this situation should be classified as VOR. For example, this situation could simply be attributed to EOG bias drift. If it could be determined that the bias was not drifting at that moment, then this could be ruled out and a better decision could be made than if VOR detection and EOG calibration were completely decoupled. In one embodiment, such uncertainties may be balanced and simultaneously considered.

At 530, the eye movement data is calibrated based on the head movement data using the algorithms stored in memory 320. The algorithms correspond to one or more probabilistic, statistical, stochastic and/or other models implemented by the calibration engine. In one embodiment, the calibration involves correlating the eye movement data with the head movement data while a vestibulo-ocular reflex (VOR) is taking place. Once the eye movement data has been calibrated based on the head movement data, the eye movement data may provide a more accurate indication of the eye movement that actually took place. Embodiments of the calibration performed by the calibration engine and the models that may be used are discussed in greater detail below.

At 540, an eye angle measurement is generated based on the calibrated eye movement data. In one embodiment, the eye angle measurement may be a displacement measurement calculated based on equations to be described in greater detail below.

Figure 5B:
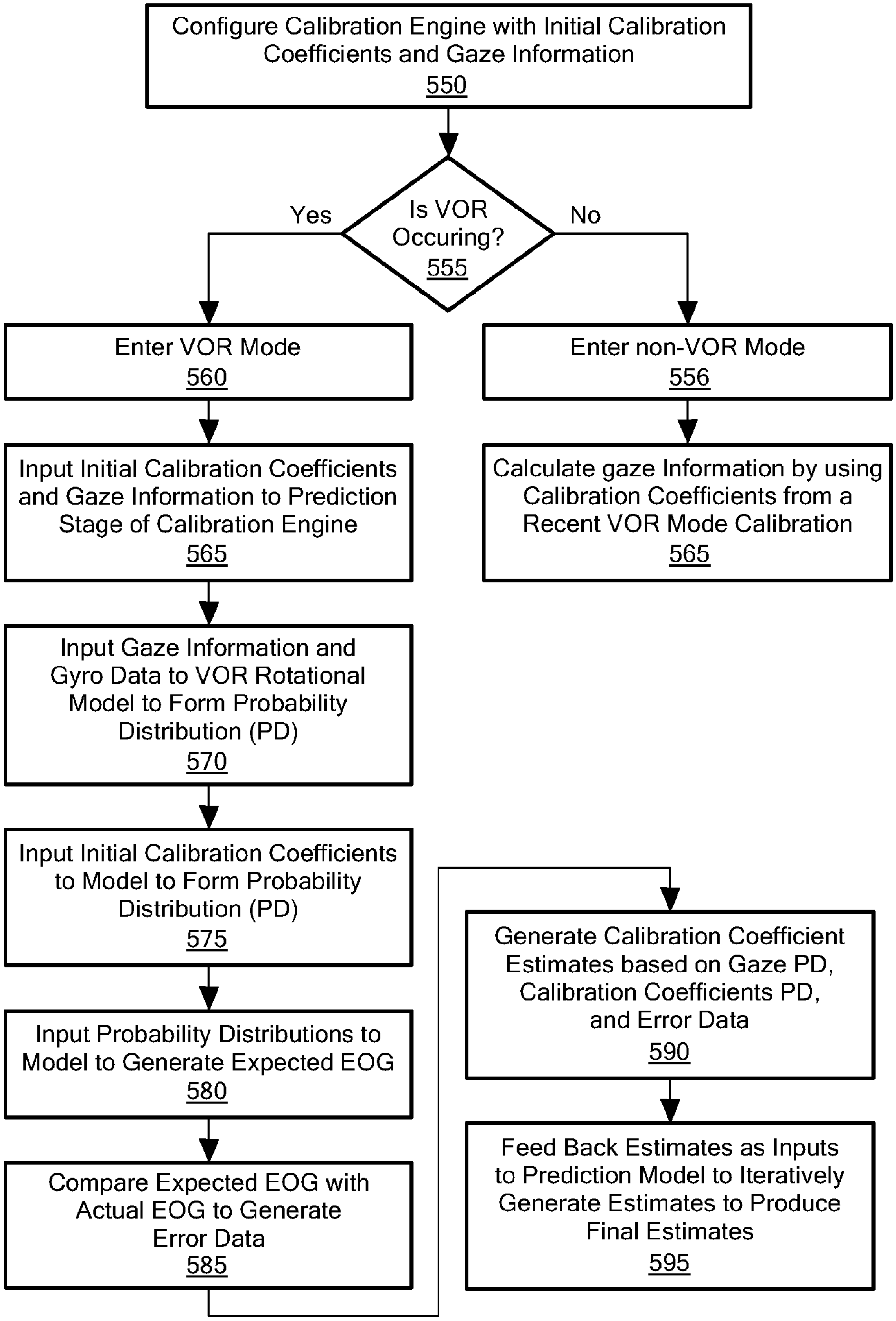
FIG. 5B shows an embodiment of a method for calibrating eye state data.

FIG. 5B shows another embodiment of a method of calibrating eye state data based on head state data acquired during a period when a vestibulo-ocular reflex is taking place. This embodiment may be considered to be one implementation of the method of FIG. 5A or may be considered independently from that method.

It should be appreciated that the described system/techniques collect eye and head data, but head data is most useful when VOR is activated.

Referring to FIG. 5B, the method includes, at 550, configuring one or more models of the calibration engine 310 with an initial set of eye state values and at least one head state value. The initial set of eye state values may include calibration coefficients and the at least one head state value may include initial gaze information. All or a portion of these initial values may be predetermined values set in a Bayesian Updating algorithm (or model) included in an Update Stage of the calibration engine, as will be described in greater detail below. In embodiments, initial calibration coefficients may be randomly selected or assigned (e.g., the initial calibration coefficients may be the result of randomly guessing or pseudo-randomly guessing.

At 555, a determination is made as to whether VOR is occurring in the subject being monitored. This determination may be made using various techniques mentioned below.

At 560, when VOR is occurring (i.e. the "yes" branch of decision block 555), the calibration engine enters a VOR mode in which the calibration model is configured with certain signal processing pathways in preparation for generating calibrated coefficients (which correspond to the calibrated eye data) and updated gaze information. This configuration operation may include, for example, modifying the calibration engine to have a first arrangement of models, e.g., this may involve connecting one or more models to the processing pathway of the calibration engine and disconnecting one or more other models. Thus, processing blocks 560-595 correspond to or occur during a calibration period. Example embodiments will be discussed in greater detail below.

At 565, an iterative process is performed where the initial set of calibration coefficients and/or the initial gaze information (set, for example, in the Bayesian Updating model) are iteratively updated using one or more probabilistic models, based on received head state information (e.g., gyroscope data). This iterative process includes inputting the initial calibration coefficients and the initial gaze information into a Prediction Stage of the calibration engine.

At 570, the gaze information is input into a VOR rotational model along with gyroscope data measuring the head state of the subject. This model outputs a probability distribution (PD) of the rotational state of the head of the subject. The estimate may be, for example, in the form of a probability distribution.

At 575, the calibration coefficients are input into another probabilistic model (e.g., a Brownian model), which modifies the coefficients in the form of a probability distribution (PD), details of which are described in greater detail below.

At 580, the probability distributions (PD) generated by the models are input into an Update Stage of the calibration engine. In this stage, an EOG dipole model generates an EOG (e.g., an expected or estimated EOG) based on the probability distributions output from the Prediction Stage. The EOG dipole model may be various types of models, including but not limited to a hidden Markov model.

At 585, an expected EOG corresponding to the estimated calibration coefficients are compared with an actual EOG measured from the subject to generate an error data.

At 590, the Bayesian Updating model generates estimates of the calibration coefficients based on the probability distribution of the gaze information and the probability distribution of the calibration coefficients and the error data.

At 595, the estimates output from the Bayesian Updating model are fed back as inputs into the Prediction Stage and new estimates are iteratively generated in the aforementioned manner until, for example, the estimates converge to a level where the error data falls below a predetermined threshold, indicating that the calibration engine has been calibrated with a high degree of precision. Once calibrated, the subject may continue to be monitored to generate now-accurate eye state data. Because the eye state data (e.g., calibrated coefficients) are generated based on head state data (e.g., calibrated gaze), the eye state data may be considered to be linked or fused with the gaze information of the subject. A highly precise eye angle measurement may then be determined based on the calibrated eye state information, for example, to determine a health condition of the subject and/or to performing various other applications.

At 556, when VOR is not occurring, the calibration engine may enter a non-VOR mode (i.e. the "No" branch of decision block 555 leads to a "use" period or a "use" mode. During this mode, the calibration engine is configured to include a second arrangement of models to establish its processing pathway. In the second arrangement, the VOR rotational model may not be connected (or activated) in the processing pathway. The second arrangement of models in non-VOR mode may therefore be different from the first arrangement of models in the VOR mode, but some of the models may be the same in one or more embodiments.

At 557, operating in non-VOR mode, the calibration engine iteratively generates estimates from the initial set of calibration coefficients using one or more probabilistic models, but without consideration of head rotation. In performing the iterations, a probabilistic model may replace the VOR rotational model in the Prediction Stage for purposes of generating probability distributions for the initial gaze information and its subsequent estimates. Estimates of the calibration coefficients are also generated with each iteration. The operations of the Update Stage, however, may be similar to the operations performed in VOR mode. In one embodiment, non-VOR operation may be considered optional.

Figure 6A:
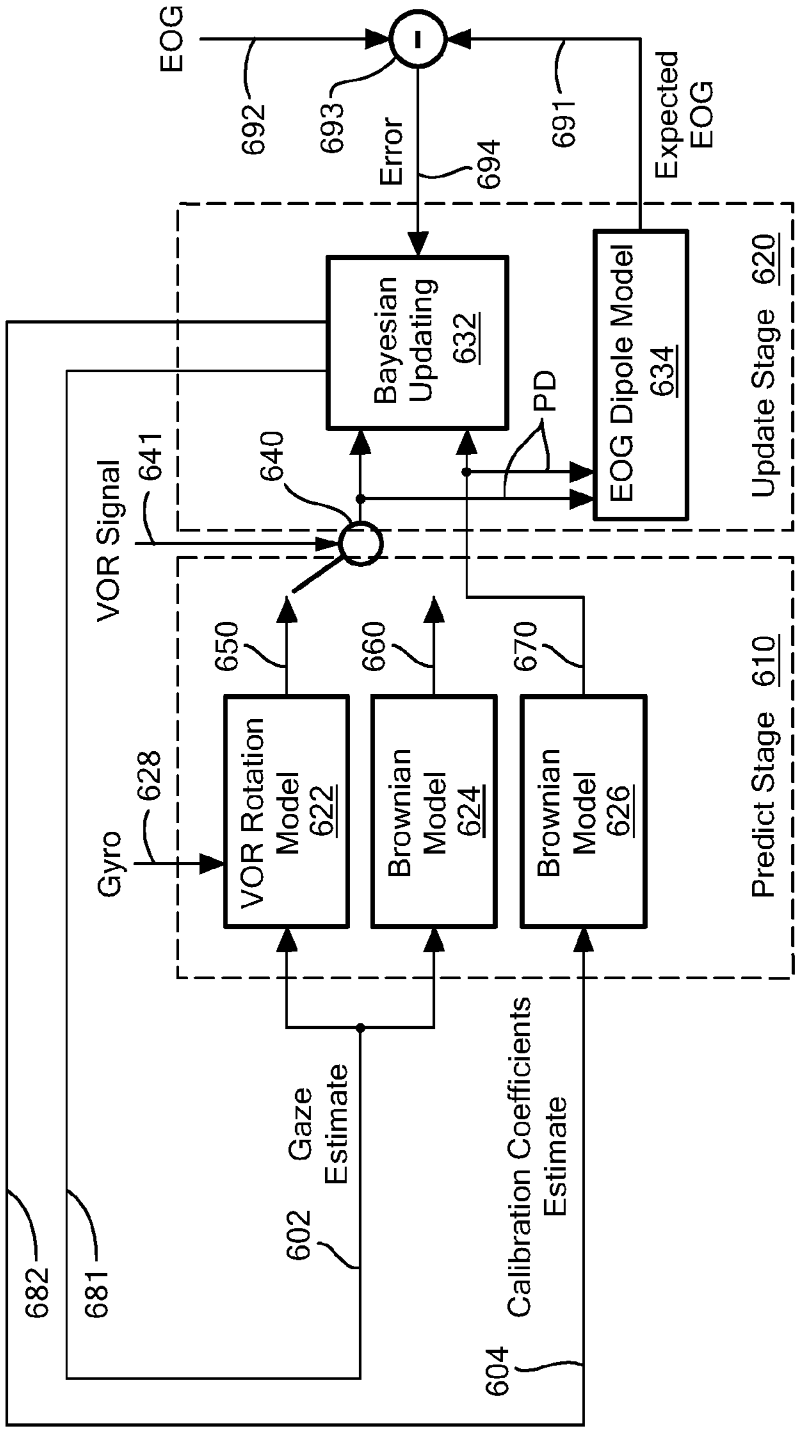
FIG. 6A shows a block diagram of an embodiment of a calibration engine.

FIG. 6A shows an embodiment of a system 600 for calibrating eye state data, e.g., EOG. The system 600 may be considered, for example, an implementation of the calibration engine 310 in the system of FIG. 3 or may be considered to be an implementation independent from that system. In addition, the system of FIG. 6A may implement any of the method embodiments described herein, including but not limited to the methods of FIGS. 5A and 5B. For illustrative purposes, the eye state data being calibrated is discussed as including electrooculography data, and it will be assumed that system 600 is one example implementation of at least the calibration engine 310 of system 300.

Referring to FIG. 6A, the system 600 (which may sometimes be referred to as a state estimation system) includes two interrelated stages: a Prediction Stage 610 and an Update Stage 620. All or a portion of these stages may be implemented by the calibration engine executing instructions and algorithms stored in memory 320 (FIG. 3). The operations performed by these stages generate eye state data that is calibrated based on head state data during a period when VOR is taking place in the subject and, in some embodiments, also when VOR is not taking place.

Initially, the Prediction Stage 610 of the calibration engine receives eye state data derived from the Update Stage 620. In one embodiment, this eye state data may correspond to a predetermined initial values set in the Bayesian Update algorithm of the Update Stage 620. For example, the initial set of eye state data may include initial gaze information 602 and a set of initial calibration coefficients 604 (also sometimes referred to as model coefficients). After the first iteration of the calibration engine, estimated eye and head state data are continuously generate, e.g., undergo continual transformation, through operations of the Prediction Stage 610 and the Update Stage 620.

The gaze information (e.g. gaze estimate) 602 indicates the direction in which the eye of the subject is looking. The direction may be expressed as two or three values in a three-dimensional reference field relative to the head of the subject and a point, e.g., point 430 in FIG. 4. In some embodiments, the eye direction (or gaze) may be generated as a result of the subject looking from one point to another point (e.g., or movement of the gaze from one location to another). The estimated gaze information is continuously generated based on feedback connecting the output of the calibration engine to its input stage. A switch 640 determines how the gaze information will be used in generating updated estimates of eye state data. Operation of the switch 640 may be based on a control signal that indicates whether VOR is happening or not, e.g., whether the calibration engine is to operate in VOR mode or non-VOR mode as previously described. The Prediction Stage 610 also received data from the gyroscope 628 to be used in a manner described herein.

In one embodiment, the voltage signals received by the EOG equipment may not be in a form that makes the gaze (eye direction) immediately apparent. In this case, the processor of the calibration engine (or the sensors themselves) may pre-process the voltage signals to generate an estimate of the eye direction and include that estimate in the gaze information 602. This may involve, for example, performing an approximate inference on the probabilistic models of the calibration engine. Examples include, but are not limited to, Kalman filtering, unscented Kalman filtering, and particle filtering. However, it should be understood that any method for approximate inference on the probabilistic model may be used.

After the first iteration, the calibration coefficients 604 correspond to estimates used to calibrate the calibration engine. For example, during calibration, all or a portion of the calibration coefficients may be adjusted or changed by one or more of the subsequent stages to generate a set of converging set of coefficients corresponding to calibrated eye state data. In one embodiment, the coefficient values may be continuously updated by the Bayesian Updating algorithm of the Update Stage 620.

The Prediction Stage 610 may include one or more dynamic models that generate outputs based on one or more variables, the gaze information 602 and the model coefficients 604. In this embodiment, the models includes a VOR rotation model 622, a first probabilistic or stochastic model 624, and a second probabilistic or stochastic model 626. In one embodiment, these models may independently operate in the processing path of the calibration engine to generate respective probability distributions.

The VOR rotation model 622 continuously generates head state information based on two inputs, namely the gaze information 602 and head state data 628 output from the head state sensor. The head state data may be indicative of head movement (and/or position) of the subject, and the head state sensor may be, for example, the gyroscope (Gyro) as previously discussed. The head state sensor may be a different type of sensor in another embodiment. The head state information and the gaze information 602 and the model coefficients 604 may all be generated simultaneously when the subject is exhibiting VOR.

Based on the gaze information 602 and the head state data 628, the VOR rotation model 622 may continuously generate information indicative of the head movement (rotation) that took place during VOR. In one embodiment, the model is a probabilistic model represented as $p(g'|g,r,w)$ which is indicative of a probability distribution of head state (e.g., type and/or extent of rotation of the head) output from the VOR rotation model 622. The variables of this model include g which represents the current gaze estimate, r which may be expressed as a binary value (logical 0 or 1) indicating whether VOR is occurring, and w which represents the angular velocity of the head of the subject as determined by the head state sensor, e.g., gyroscope. Based on the probability distribution, head state information 650 (in the form of an updated gaze estimate g') is output from the Prediction Stage for use by the Update Stage during VOR.

The first probabilistic or stochastic model 624 may continuously generate the probability distribution of the gaze estimate 660. Because the model is continuously operating (based on the feedback loops), model 624 continuously generates the probability distribution of the gaze estimate at the next time step (e.g., an updated gaze estimate) based on the current gaze estimate fed back from the Bayesian updating algorithm along feedback path 681.

An example of model 624 is a Brownian model that continuously generates a probability distribution represented as $p(g'|g,A,b)$, where g represents the current gaze estimate input (or fed back from the output of the calibration engine), A and b represent current (or fed back) calibration coefficients, and g' represents an updated gaze estimate as output from model 624. Any approximate inference method (or model) can be used to "predict" an updated gaze estimate g' using current gaze estimate g. For example, the mean and variance can be tracked (e.g., as is done in Kalman filtering) or many randomly drawn samples can be propagated (e.g., as is done in particle filtering). However, these types of filtering are merely examples. An embodiment of how the mean and co-variance are computed for the gaze estimates is described in greater detail below.

While models 622 and 624 are continuously operating, the output of only one of the models is output to the Output Stage 620 at a given time. Which output is received by the Output Stage 620 may be controlled by the VOR switch 640. The VOR switch may be controlled, for example, based on a control signal (VOR signal) 641 output from the processor of the calibration engine. The value of the control signal may control the position of the switch 640. When the processor determines that VOR is occurring, the value of variable r=1 and the switch connects the output of the VOR rotation model 622 to the Update Stage 620. When the processor determines that VOR is not occurring, the value of variable r=0 and the switch connects the output of the first probabilistic model 660 to the Update Stage 620.

The second probabilistic or stochastic model 626 may continuously generate probability distributions of the calibration coefficients A and b. Because the model 626 is continuously operating (based on the feedback loops), the model continuously generates the probability distribution of the calibration coefficients at the next time step (e.g., updated estimates for the calibration coefficients) based on the current estimates of the calibration coefficients fed back from the Bayesian updating algorithm along feedback path 682. An example of model 626 is a Brownian model that continuously generates a probability distribution represented as p(A'A) and p(b'|b), where A is a first one of the calibration coefficients and b is a second one of the calibration coefficients. More specifically, A represents a current (or fed back) estimate of the first calibration coefficient, A' represents an updated estimate of the first calibration coefficient output from the model, b represents a current (or fed back) estimate of the second calibration coefficient, b' represents an updated estimate of the second calibration coefficient output from the model. These estimates are output to the Update Stage 620.

As with model 624, any approximate inference method (or model) can be used to "predict" the estimates for the updated calibration coefficients A' and b' using current calibration coefficient estimates. For example, the mean and variance can be tracked (e.g., as is done in Kalman filtering) or many randomly drawn samples can be propagated (e.g., as is done in particle filtering). However, these types of filtering are merely examples. An embodiment of how the mean and co-variance are computed for the calibration coefficient estimates is described in detail below.

The Update Stage 620 correlates the eye state data (e.g., gaze and calibration coefficient estimates) with the head movement data output from the Prediction Stage 610. When the VOR switch 640 connects the VOR rotation model 622 to the Update Stage 620, the eye state data is correlated with the head movement data during VOR. When the VOR switch 640 connects the first probabilistic mode 624 to the Update Stage 620, the eye state data is correlated with the head movement data during a time when VOR is not occurring.

The Update Stage 620 includes an EOG dipole model 632 and the Bayesian Updating algorithm 634 previously discussed. In one embodiment, the Bayesian updating algorithm may be a recursive Bayesian algorithm executed by the processor of the calibration engine. This algorithm, or machine-learning model, may generate updated estimates of the head state data and the eye state data, which respectively may be expressed as the gaze estimates and calibration coefficient estimates output from the Prediction Stage 610. Because the calibration engine has an iterative architecture (based on feedback paths 681 and 682), the estimates may be continuously generated, whether VOR is occurring or not. In another embodiment, the calibration engine may be modified with instructions that control specific circumstances when continuously calibration occurs. These circumstances may be time-driven or event-driven, or both.

The EOG dipole model 632 generates expected EOG data 691 based on the current gaze estimates and current calibration coefficient estimates output from the Prediction Stage 610. In one embodiment, the EOG dipole model 632 may be a probabilistic model that generates a probability distribution corresponding to the expected EOG data. The probabilistic model may be expressed as p(v|g,A,b), wherein v represents the expected EOG data generated based on g representing the gaze estimate and A and b representing the calibration coefficients output from the Prediction Stage 610. Examples of mean and covariance for the distribution output from model 632 are discussed below. The EOG dipole model may be a Markov model or another type of probabilistic model.

Once generated, the expected EOG data 691 may be compared with reference EOG data 692 (e.g., produced by an actual EOG measurement) using difference logic 693. The difference logic generates error data 694 that is input into the Bayesian Updating algorithm 634. The Bayesian algorithm generates updates estimates of the gaze estimate and calibration coefficients (which, for example, may also be referred to as head state data and eye state data, respectively) based on the error data 694. The updated estimates are fed back through paths 681 and 682 for input into the Prediction Stage 610. Through this iterative process, the gaze estimates and calibration coefficients and continuously generated so that they converge to the true gaze and calibration coefficients.

In one embodiment, the EOG data 691 and the difference logic 693 may only be used in a training phase of the models of the calibration engine. During use monitoring, the models may be considered to be trained and the expected EOG data 691 may be considered to correspond to the calibrated eye state data. This EOG data may be stored in data storage 330, output for display or additional processing, and/or output to an internal or external processor which, for example, may be used to determine a health condition of the subject.

Calculations performed by the calibration engine may expressed mathematically in the following example embodiment. The models of this embodiment may correspond, for example, to the models used by the calibration engine of FIG. 3.

In this embodiment, a two-channel EOG and a three-axis gyroscope are attached to the head of a subject to be monitored. The head state data generated by the gyroscope is input into the Prediction Stage 610 of the calibration engine. The Bayesian Updating algorithm (or model) 634 may output an initial set of predetermined gaze and calibration coefficients along the feedback paths. Alternatively, the initial coefficients may be input into the Prediction Stage 610 (e.g., by the calibration engine processor) along a path that bypasses the Bayesian Updating algorithm 634.

In this embodiment, EOG calibration and gaze estimation are performed jointly as approximate inference on a hidden Markov model. This model may be used to implement one or more of the probabilistic models in the Prediction Stage or the EOG dipole model in the Update Stage. An example of stochastic variables of the model is shown in Table 1. Each of these variables may be a function of time and an underlying probability space. The unit-sphere S2 is represented as $\{g \in \mathbb{R}^3 \langle g|g=1\rangle\}$. When the VOR of the subject is engaged, r=1. Otherwise r=0.

TABLE 1

| Variable | Symbol | Range |
|---|---|---|
| Gyroscope Angular-Velocity Reading | ω | $R^3$ |
| Gaze Direction (in gyroscopic coordinates) | g | $S^2$ |
| EOG Projection Matrix | A | $R^{2\times 3}$ |
| EOG Bias Vector | b | $R^2$ |
| EOG Voltage Readings | v | $R^2$ |
| VOR Activity Boolean | r | {0, 1} |

In applying the hidden Markov model, time is discretized into increments of a predetermined time duration, given, for example, as $\nabla t \in \mathbb{R}+$, dictated by sampling rate the sampling rate of the gyroscope used to capture the head state data.

Figure 6B:
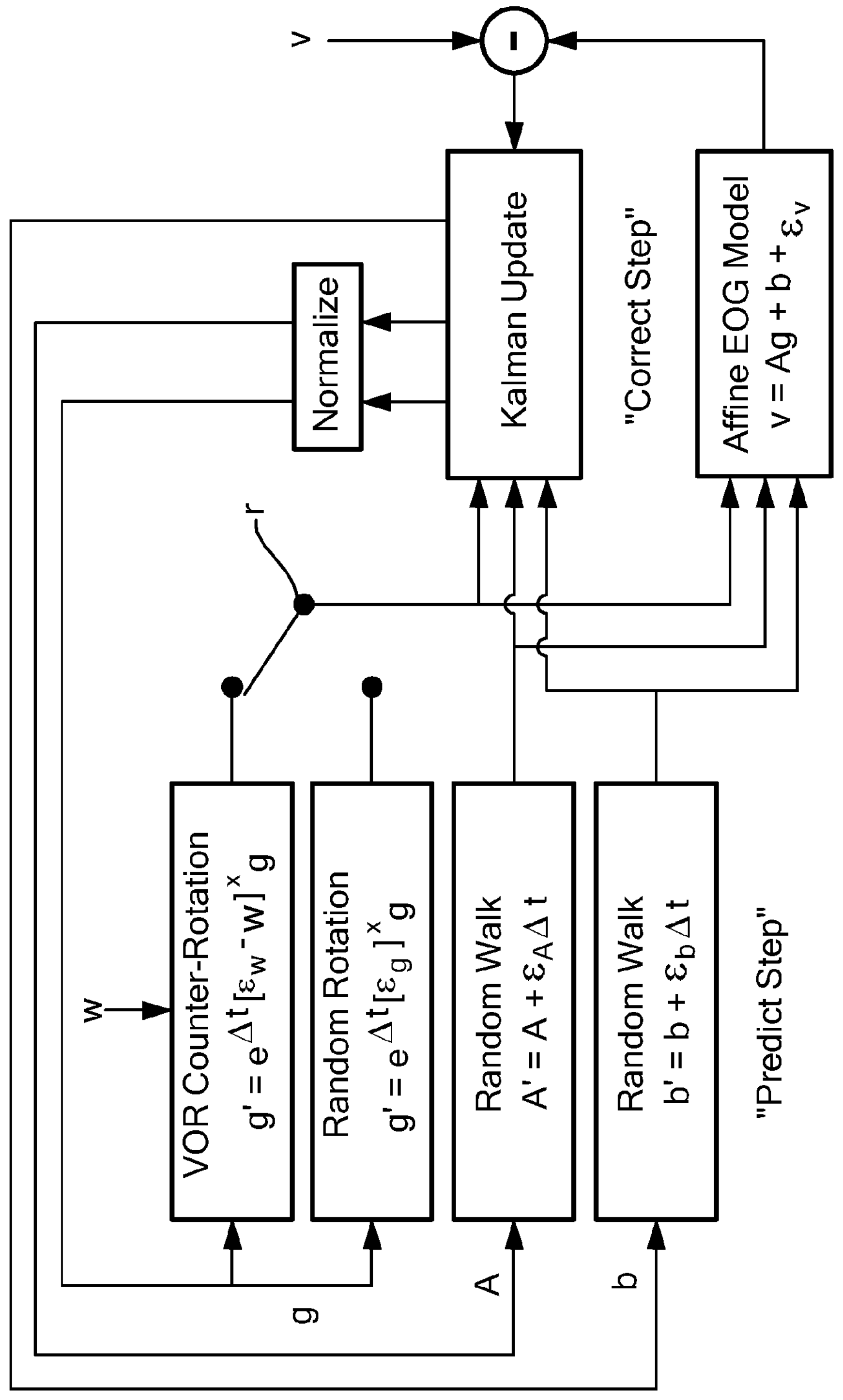
FIG. 6B shows an embodiment of a calibration engine.
Figure 7:
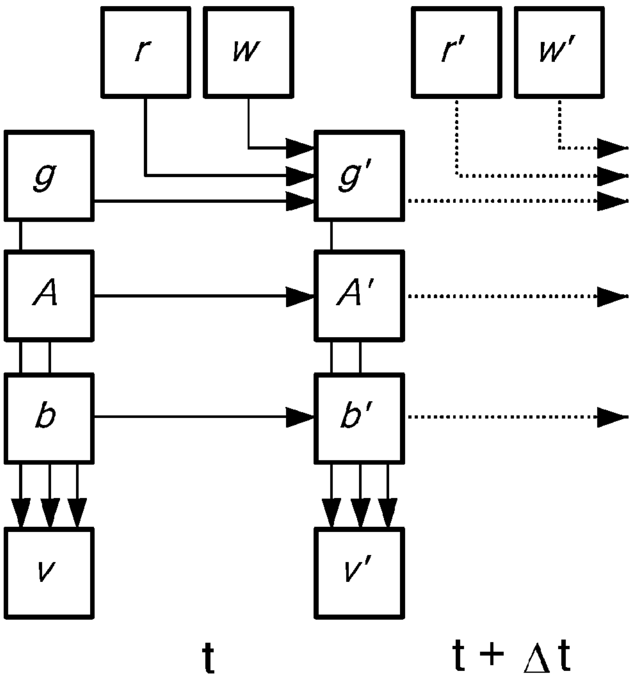
FIG. 7 shows an embodiment of operations for calibrating eye state data.

FIG. 7 shows a logical diagram indicative of operations performed by a computer model that may be used to perform the Bayesian Updating operation (e.g., based on a Recursive Bayesian estimation algorithm) in the calibration engine of FIG. 6. In FIG. 7, each node represents a variable as defined in Table 1, and each arrow represents a conditional dependency indicated in Table 2. The shaded nodes correspond to the "hidden" states that are to be inferred, while the clear nodes are observed. The dotted arrows indicate that this structure repeats for all time-steps (t+n∇t∀n∈N).

Moreover, FIG. 7 shows an example of relationships that may exist between the model variables across each time-step (or iteration). In this case, a first set of variables is shown at time t and changes in these variables (indicated by the prime symbol "'") are shown at a subsequent time increment ∇t, e.g., at time t+∇t. The meaning of these variables are indicated in Table 1.

The variable g represents gaze direction expressed in gyroscope coordinates. As shown by horizontal arrows 710, the gaze direction of the subject changes based on gyroscope angular-velocity readings (ω) and whether or not the subject is experiencing VOR (r). In one embodiment, whether or not the subject is experiencing VOR at any given time may be determined as an observable/known. In another embodiment, it is possible to extend this framework to the case where r is another hidden state.

As shown by horizontal arrows 720 and 730, the EOG calibration coefficients (A and b) are assumed to change independently of the gaze direction and of each other. In some cases, the drift of these coefficients may be governed by changes in electrode-skin impedance and the adaptive state of the eye rather than gaze direction changes or head movement. Corrections may be performed, for example, by the Bayesian updating of FIG. 6.

As shown by vertical arrows 740, the calibrated eye state data (e.g., EOG voltage readings (v)) at each time-step are probabilistically specified by the gaze direction and EOG calibration coefficients at that same time-step, which, for example, mirror the operations performed by the calibration engine 610 of FIG. 6. Table 2 provides an example of parameters which may be used as a basis for modeling corresponding conditional probability distributions as Gaussians, along with equations indicating how corresponding mean and covariance values are calculated. In Table 2, The operator [ω]X expresses a 3-dimenational vector as a skew-symmetric matrix, the exponential (x) of which may be computed efficiently, for example, based on Rodrigues'Rotational Formula.

TABLE 2

| Gaussian | Mean | Covariance |
|---|---|---|
| p(g'\|g, r, ω) | $e^{-r\Delta t[\omega]^x} g$ | $(rC_\omega + (1-r)C_g)\Delta t$ |
| p(A'\|A) | A | $C_A\Delta t$ |
| p(b'\|b) | b | $C_b\Delta t$ |
| p(v \|g, A, b) | Ag + b | $C_v$ |

In the first row of Table 2, a conditional probability p is given of the gaze direction of the subject, which changes based on gyroscope angular-velocity readings (ω) and whether or not the subject is experiencing VOR (r). The first row also gives equations for mean and covariances for the gaussian variables.

The conditional probability distribution of g' switches over time between two modes, a first mode where the subject is experiencing VOR and a second mode where the subject is not experiencing VOR. Referring to FIG. 6, the Update Stage includes or is coupled to a logical switch 640 that is set to different positions based on whether the first mode or the second mode exists. When the first mode exists, the switch 640 is connected (e.g., by a first control signal generated by processor 315) to the VOR rotation model 622 and the eye state data is generated based on the head state data to generate calibrated eye state data. When the second mode exists, the switch 640 is set (e.g., by a second control signal generated by processor 315) to the first probabilistic (e.g., Brownian) model 624 and no calibration is performed. The first control signal may correspond to variable r=1 and the second control signal may correspond to variable r=0.

When r=0, then the change in gaze may be modeled as a random-walk of covariance Cg∇t, which may effective serve as a tuning knob to smooth-out gaze trajectories by controlling how much probability is placed on large gaze changes between time-steps.

When r=1, then the gaze is assumed to counter-rotate the angular-velocity measured by the gyroscope. The uncertainty in this relationship may be encoded by the covariance $C_\omega$ and is due to inherent noise and bias of the gyroscope, as well as an ignored transient lag of the VOR and translations of the eyeball. The trace of $C_\omega$ may be significantly less than the trace of Cg in some cases.

Because variable g may be defined to have a unit-norm, the Gaussian form of p(g'|g,r, ω) may only be reasonable for small ∇t increments. In one embodiment, a Kent-like distribution may be used instead by explicitly introducing a Gaussian variable η for the gaze process noise and specifying p(g'|g, r, ω) indirectly based on the following equation:

$$g' = e^{-r\nabla t[\omega-\eta]^{\wedge}x} g.$$

In the second and third rows of Table 2, conditional probabilities p are given of the eye state (or EOG) calibration coefficients A and b, respectively. The second and third rows also give equations for mean and covariances for eye state calibration coefficients A and b.

In the fourth row of Table 2, a conditional probability p is given for the calibrated eye state data (e.g., EOG voltage readings (v)), along with equations for mean and covariance for these readings v.

The EOG calibration coefficients A and b may be modeled as random-walks of covariance CA∇t and Cb∇t, respectively. The mean of p(v|g, A, b) may essentially define the purpose of A and b in the model. In one embodiment, these variables may determine an affine transformation of the gaze that is read by the EOG (with noise of covariance Cv). Thus, in this embodiment, the electrical properties of the dipole of the eye and the EOG may all be encoded by the variables A and b.

In one implementation, all sources of uncertainty may be modeled as white for simplicity and to avoid potential unobservabilities. However, if any analysis points to a more accurate spectrum, the model can easily be colored by augmenting it, for example, with auxiliary states that follow an Ornstein-Uhlenbeck process.

As posed, the only state nonlinearity in the model may be the product of A and g in E[v|g, A, b]. Thus a nonlinear extension of the Kalman Filter may be used for performing approximate inference of the hidden states in some embodiments. The filter may be, for example, an Extended Kalman Filter, an Unscented Kalman Filter, or a Rao-Blackwellized Particle Filter. In some implementations, sufficient results may be obtained with an Extended Kalman Filter. In one embodiment, an additional operation of renormalizing g may be performed after each Kalman-update by, for example, by "shedding" its magnitude onto A in the following manner:

$$s = norm(g)$$

$$g/ = s$$

$$A^{*} = s$$

Once the hidden state trajectory has been inferred for a given EOG-gyroscope time-series, a point-estimate of the angular displacement of any eye movement (saccade or otherwise) may be computed based on the following equation:

$$\hat{\delta}_{tr} = \cos^{-1}\langle\hat{g}(t), \hat{g}(\tau)\rangle$$

where ĝ is the mode of the inferred posterior distribution over gaze, and t through t is the time interval of the movement. Angular displacements of the eye (e.g., eye angle measurements) may be more useful than the gaze direction vector in some applications because the gaze direction vector is expressed in the coordinates of the inconsistently mounted gyroscope. The angular displacement measurements may provide consistent, meaningful features for physiological analysis over time and across subjects.

Figure 8:
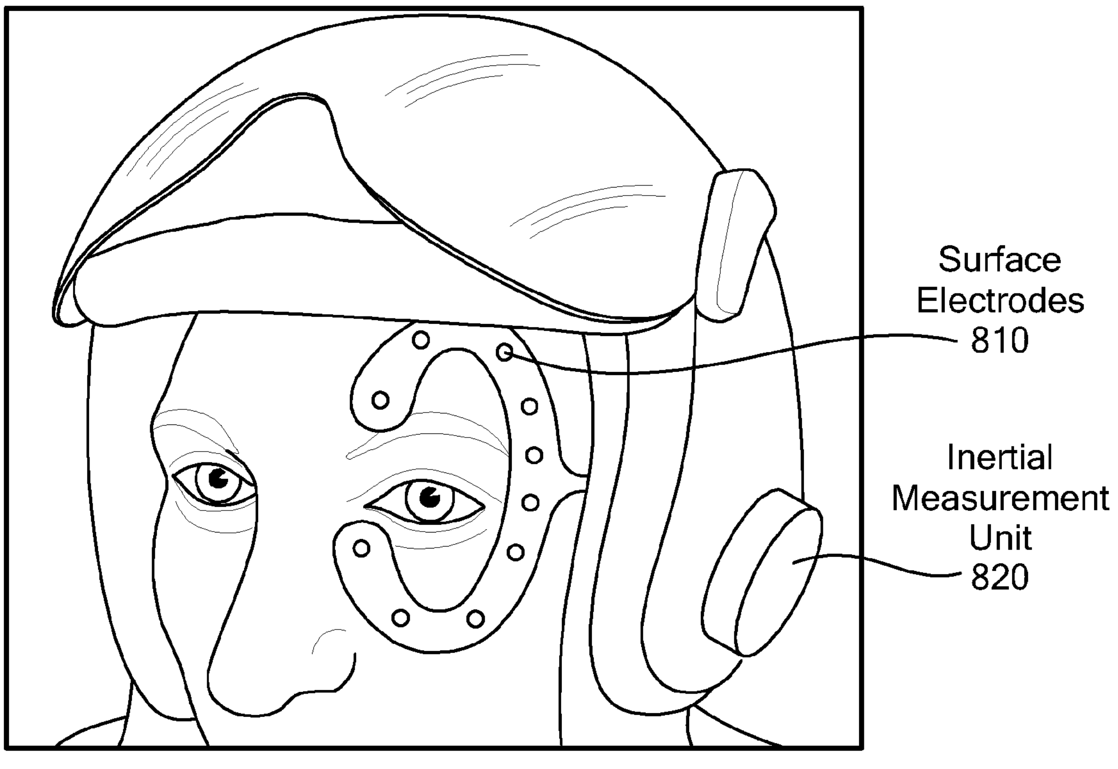
FIG. 8 shows an embodiment of a system for acquiring eye state data and head state data.

FIG. 8 shows an embodiment of system 800 which includes an eye sensor 810 and inertial measurement sensor 820, which may be used to generate the input signals of the calibration engine described herein. The eye sensor includes an arrangement of surface electrodes 811 in an area in an eye area of a subject. The electrodes are coupled to a support 812, which is adhered or otherwise coupled to the skin. When the support is positioned in the eye area, the electrodes are at desired positions relative to the eye, in order to capture potentials in a continuous manner over time, e.g., over the calibration period. The potentials may be compared to generate voltages indicative of eye state data (e.g., EOG signals), which may be correlated to head state data during VOR for purposes of calibrating the eye state data.

The inertial measurement sensor 820 is coupled to or integrated within a helmet 821. When worn by the subject, the sensor 820 is set at a predetermined position on the head, deemed suitable for capturing accurate head state data, as mentioned above. The inertial measurement sensor may include a gyroscope (as previously discussed) or another type of device for measuring head movement or the lack thereof.

The system of FIG. 8 and the manner in which it is operated outperforms other sensor systems in a number of ways. For example, system 800 may have lower size, weight, and power requirements than video-based systems, EOG-type glasses, and other sensor systems. System 800 is also not bulky and has a low profile, making it suitable for use in the field or free-living conditions outside of a clinical setting. In addition, eye sensor 810 attaches to the skin which makes it robust to motion. Unlike all other systems, system 800 performs automatic recalibration in accordance with the embodiments described herein, making it far more accurate and reliable than other systems for purposes of generating eye state data and eye angle measurements, and performing health condition assessments. Moreover, system 800 has a pupillometry capability that measures data based on pupillary light reflex.

One or more of the aforementioned embodiments provide a variety of innovations in the technical field of health management, including but not limited to various electooculography applications. These embodiments include a system and method are provided for calibrating eye state data based on head state data during a time when a vestibulo-ocular reflex is taking place in a subject. The eye state data may include eye movement data, and the head state data may include head movement data. The movements may include rotations of the eye and head. Through this calibration system and method, a more accurate and reliable indication of eye state may be determined in a manner that is less costly than other methods.

Moreover, calibration of the eye state data may be performed in free-living conditions, where the physiological behavior of a subject is more likely to be realistic. The free-living conditions may include use in mobile environments or rugged field conditions, such as when a test subject is walking, driving, or engaging in other everyday activities. Use of the system and method under these conditions may give a truer reading of eye movement, which may translate into more accurate health assessments. Other electrooculographic methods do not provide an indication of eye movement in so-called free-living conditions, making them impractical as a preventative health tool and for real-time monitoring applications.

Moreover, one or more of the system and method embodiments may be performed by the subject without supervision or implementation by health professionals and without having to perform the measurements in a controlled medical setting such as a diagnostic center, doctor's office, or hospital.

Moreover, calibration of the eye state data may be performed in a continuous manner over a predetermined period, which may include times when VOR is taking place and when VOR is not taking place. Thus, unlike other methods which are applicable only to discrete periods of time, one or more of the system and method embodiments may generate a more accurate calibration in a way that is not intrusive on the time and convenience of the subject.

Moreover, one or more of the system and method embodiments may not have the same shortcomings as video eye trackers, but may still maintain the ability to generate improved quality of data for clinical, commercial, operational, and research use.

Moreover, one or more of the system and method embodiments eliminate the need for independent references, while retaining the ability to extract high precision eye angle measurements though time.

Moreover, by calibrating EOG signals, the angular rotation of eye movements (an invariant measure) generated by one or more of the system and method embodiments can be determined instead of just measuring voltage changes (arbitrary measure).

Moreover, in view of these and other technological innovations, one or more of the system and method embodiments are suitable for a variety of applications not directly related to clinical and health monitoring uses. These applications include, but are not limited to, gaming, personal fitness, and military performance applications.

The methods, processes, and/or operations described herein may be performed by code or instructions to be executed by a computer, processor, controller, or other signal processing device. The computer, processor, controller, or other signal processing device may be those described herein or one in addition to the elements described herein. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods described herein.

The processors, logic, switches, models, engines, estimators, and other signal generating and signal processing features of the embodiments described herein may be implemented in non-transitory logic which, for example, may include hardware, software, or both. When implemented at least partially in hardware, the processors, logic, switches, models, engines, and other signal generating and signal processing features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the processors, logic, switches, models, engines, and other signal generating and signal processing features may include, for example, a memory or other storage device for storing code or instructions to be executed, for example, by a computer, processor, microprocessor, controller, or other signal processing device. The computer, processor, microprocessor, controller, or other signal processing device may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

Also, another embodiment may include a computer-readable medium, e.g., a non-transitory computer-readable medium, for storing code or instructions for implementing the operations described above. The computer-readable medium may be a volatile or non-volatile memory or other storage device, which may be removably or fixedly coupled to the computer, processor, controller, or other signal processing device which is to execute the code or instructions to perform the method embodiments or operations of the apparatus embodiments described herein.

An appendix is included with this specification and is included as part of the specification. The Appendix provides additional supporting information relating to and describing the embodiments described herein.

Any reference in this specification to an "embodiment" means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments. The features of any one embodiment may be combined with features of one or more other embodiments described herein to form additional embodiments.

Furthermore, for ease of understanding, certain functional blocks may have been delineated as separate blocks; however, these separately delineated blocks should not necessarily be construed as being in the order in which they are discussed or otherwise presented herein. For example, some blocks may be able to be performed in an alternative ordering, simultaneously, etc.

Although the present invention has been described herein with reference to a number of illustrative embodiments, it should be understood that numerous other modifications and embodiments can be devised by those skilled in the art that will fall within the spirit and scope of the principles of this invention. More particularly, reasonable variations and modifications are possible in the component parts and/or arrangements of the subject combination arrangement within the scope of the foregoing disclosure, the drawings and appended claims without departing from the spirit of the invention. In addition to variations and modifications in the component parts and/or arrangements, alternative uses will also be apparent to those skilled in the art.

We claim:

1. A method for processing information, comprising:

receiving eye state data measured during one or more calibration periods in which a vestibulo-ocular reflex (VOR) occurs in a subject while viewing a target;

receiving head state data measured during the one or more calibration periods, the head state data including data corresponding to measurements of head rotation of the subject taken during the occurrence of the vestibulo-ocular reflex (VOR);

continuously, during at least one of the one or more calibration periods, calibrating the eye state data based on the head state data; and generating an eye angle measurement based on the calibrated eye state data, wherein continuously calibrating the eye state data includes correlating the eye state data with the data corresponding to the measurements of the head rotation taken during the occurrence of the vestibulo-ocular reflex.

2. The method of claim 1, wherein:

the eye state data includes eye movement data; and the head state data includes head movement data.

3. The method of claim 2, wherein correlating the eye movement data includes:

implementing at least one probabilistic model to correlate the eye state data measured during the calibration period with the head state data.

4. The method of claim 1, wherein:

the head state data includes gaze information, and the eye state data includes calibration coefficients corresponding to an eye state of the subject, wherein the eye state includes an eye position, an eye orientation, eye movement, eye blinks, or any combination thereof.

5. The method of claim 4, wherein continuously generating the eye state data includes:

(a) generating a first probability distribution based on one or more initial values of the head state data and data from a head sensor;

(b) generating a second probability distribution based on initial values of the eye state data;

(c) generating estimates of gaze and the calibration coefficients based on the first probability distribution and the second probability distribution; and (d) iteratively repeating (a) to (c) with the first probability distribution generated based on the estimate of the gaze generated in (c).

6. The method of claim 5, wherein the first probability distribution is generated using a VOR rotational model.

7. The method of claim 5, wherein continuously generating the eye state data includes:

generating an expected electrooculogram (EOG) based on the first probability distribution and the second probability distribution;

comparing the expected EOG with an actual EOG;

generating error data based on the comparison; and generating the estimates of gaze and the calibration coefficients based on the first probability distribution, the second probability distribution, and the error data.

8. The method of claim 7, wherein generating the estimates of gaze and the calibration coefficients is performed by a Bayesian Updating method.

9. A system for processing information, comprising:

a storage area configured to store instructions; and a processor, operatively coupled to the storage area, configured to execute the instructions to:

receive eye state data measured during one or more calibration periods in which a vestibulo-ocular reflex (VOR) occurs in a subject while viewing a target;

receive head state data measured during one or more calibration periods, the head state data including measurements of head rotation of the subject taken during the occurrence of the vestibulo-ocular reflex (VOR);

continuously, during at least one of the one or more calibration periods, calibrate the eye state data based on the head state data; and generate an eye angle measurement based on the calibrated eye state data, wherein the processor is configured to continuously calibrate the eye state data by correlating the eye state data with the data corresponding to the measurements of the head rotation taken during the vestibulo-ocular reflex.

10. The system of claim 9, wherein:

the eye state data includes eye movement data; and the head state data includes head movement data.

11. The system of claim 10, wherein the processor is configured to correlate the eye movement data by implementing at least one probabilistic model to correlate the eye state data measured during the calibration period with the head state data.

12. The system of claim 9, wherein:

the head state data includes gaze information, and the eye state data includes calibration coefficients corresponding to eye state of the subject, wherein the eye state includes an eye position, an eye orientation, eye movement, eye blinks, or any combination thereof.

13. The system of claim 12, wherein the processor is configured to continuously generate the eye state data by:

(a) generating a first probability distribution based on one or more initial values of the head state data and data from a head sensor;

(b) generating a second probability distribution based on initial values of the eye state data;

(c) generating estimates of gaze and the calibration coefficients based on the first probability distribution and the second probability distribution; and (d) iteratively repeating (a) to (c) with the first probability distribution generated based on the estimate of the gaze generated in (c).

14. The system of claim 13, wherein the processor is configured to generate the first probability distribution using a VOR rotational model.

15. The system of claim 13, wherein the processor is configured to continuously generate the eye state data by:

generating an expected electrooculogram (EOG) based on the first probability distribution and the second probability distribution;

comparing the expected EOG with an actual EOG;

generating error data based on the comparison; and generating the estimates of gaze and the calibration coefficients based on the first probability distribution, the second probability distribution, and the error data.

16. The system of claim 15, wherein the processor is configured to generate the estimates of gaze and the calibration coefficients is performed by a Bayesian Updating method.

17. A non-transitory computer-readable medium storing instructions which, when executed by one or more processors, cause the one or more processors to:

receive eye state data measured during one or more calibration periods in which a vestibulo-ocular reflex (VOR) occurs in a subject while viewing a target;

receive head state data measured during one or more calibration periods, the head state data including measurements of head rotation of the subject taken during the occurrence of the vestibulo-ocular reflex (VOR);

continuously, during at least one of the one or more calibration periods, calibrate the eye state data based on the head state data; and generate an eye angle measurement based on the calibrated eye state data, wherein the processor is configured to continuously calibrate the eye state data by correlating the eye state data with the data corresponding to the measurements of the head rotation taken during the vestibulo-ocular reflex.

18. The medium of claim 17, wherein:

the head state data includes gaze information, and the eye state data includes calibration coefficients corresponding to eye state of the subject, wherein the eye state includes an eye position, an eye orientation, eye movement, eye blinks, or any combination thereof.

19. The medium of claim 18, wherein the instructions, when executed by the one or more processors, cause the one or more processors to:

(a) generate a first probability distribution based on one or more initial values of the head state data and data from a head sensor;

(b) generate a second probability distribution based on initial values of the eye state data;

(c) generate estimates of gaze and the calibration coefficients based on the first probability distribution and the second probability distribution; and (d) iteratively repeat (a) to (c) with the first probability distribution generated based on the estimate of the gaze generated in (c).

20. The medium of claim 19, wherein the instructions, when executed by the one or more processors, cause the one or more processors to:

generate an expected electrooculogram (EOG) based on the first probability distribution and the second probability distribution;

compare the expected EOG with an actual EOG;

generate error data based on the comparison; and generate the estimates of gaze and the calibration coefficients based on the first probability distribution, the second probability distribution, and the error data.

* * * * *